US008894771B2

(12) United States Patent
Floyd et al.

(10) Patent No.: US 8,894,771 B2
(45) Date of Patent: Nov. 25, 2014

(54) COMPOSITIONS COMPRISING C5 AND C6 MONOSACCHARIDES

(71) Applicant: Renmatix, Inc., King of Prussia, PA (US)

(72) Inventors: Daniel Clay Floyd, Richmond, VA (US); Kiran Kadam, Golden, CO (US); Srinivas Kilambi, Marietta, GA (US)

(73) Assignee: Renmatix, Inc., King of Prussia, PA (US)

( * ) Notice: Subject to any disclaimer, the term of this patent is extended or adjusted under 35 U.S.C. 154(b) by 0 days.

(21) Appl. No.: 13/649,395

(22) Filed: Oct. 11, 2012

(65) Prior Publication Data

US 2013/0167836 A1 Jul. 4, 2013

Related U.S. Application Data

(60) Provisional application No. 61/581,907, filed on Dec. 30, 2011, provisional application No. 61/581,922, filed on Dec. 30, 2011, provisional application No. 61/581,878, filed on Dec. 30, 2011, provisional application No. 61/581,890, filed on Dec. 30, 2011.

(51) Int. Cl.
| | | |
|---|---|---|
| C13K 13/00 | (2006.01) | |
| C13B 50/00 | (2011.01) | |
| C13K 11/00 | (2006.01) | |
| C13K 1/04 | (2006.01) | |
| C07H 3/06 | (2006.01) | |
| C13K 1/02 | (2006.01) | |

(52) U.S. Cl.
CPC ............. *C13B 50/00* (2013.01); *C13K 13/00* (2013.01); *C13K 11/00* (2013.01); *C13K 1/04* (2013.01); *C07H 3/06* (2013.01); *C13K 13/002* (2013.01); *C13K 13/007* (2013.01); *C13K 1/02* (2013.01); *Y02E 50/16* (2013.01)
USPC .............................................. 127/30; 127/37

(58) Field of Classification Search
USPC ...................................................... 127/30, 37
See application file for complete search history.

(56) References Cited

U.S. PATENT DOCUMENTS

| | | | |
|---|---|---|---|
| 3,990,904 A | 11/1976 | Friese et al. | |
| 4,105,467 A | 8/1978 | Buckl et al. | |
| 4,165,240 A | 8/1979 | Enokizono et al. | |
| 5,705,369 A | 1/1998 | Torget et al. | |
| 5,980,640 A | 11/1999 | Nurmi et al. | |
| 6,022,419 A | 2/2000 | Torget et al. | |
| 6,086,681 A * | 7/2000 | Lindroos et al. | 127/37 |
| 6,872,316 B2 * | 3/2005 | Heikkila et al. | 210/652 |
| 7,026,152 B2 | 4/2006 | Ingram et al. | |
| 8,030,039 B1 | 10/2011 | Retsina et al. | |
| 2002/0153317 A1 | 10/2002 | Heikkila et al. | |
| 2005/0244934 A1 | 11/2005 | Foody et al. | |
| 2006/0281913 A1 | 12/2006 | Ferreira et al. | |
| 2007/0254348 A1 | 11/2007 | Retsina et al. | |
| 2008/0102502 A1 | 5/2008 | Foody et al. | |
| 2008/0292766 A1 | 11/2008 | Hoffman et al. | |
| 2009/0176979 A1 | 7/2009 | Hara et al. | |
| 2009/0232892 A1 | 9/2009 | Yamasaki et al. | |
| 2010/0043782 A1 | 2/2010 | Kilambi et al. | |
| 2010/0069626 A1 | 3/2010 | Kilambi | |
| 2010/0136634 A1 | 6/2010 | Kratochvil et al. | |
| 2010/0170504 A1 | 7/2010 | Zhang | |
| 2010/0184151 A1 | 7/2010 | Tolan et al. | |
| 2010/0203605 A1 | 8/2010 | Kim et al. | |
| 2010/0297704 A1 | 11/2010 | Li | |
| 2011/0183394 A1 | 7/2011 | Bell et al. | |
| 2012/0116063 A1 | 5/2012 | Jansen et al. | |
| 2012/0282655 A1 * | 11/2012 | Gibbs | 435/72 |
| 2012/0289692 A1 | 11/2012 | Gray et al. | |

FOREIGN PATENT DOCUMENTS

| | | |
|---|---|---|
| CN | 101613970 A | 12/2009 |
| EP | 814676 A1 | 1/1998 |
| EP | 1304412 A2 | 4/2003 |
| JP | 62-283988 A | 12/1987 |
| JP | 2008-035853 A | 2/2008 |
| WO | 00/61276 A1 | 10/2000 |
| WO | 01/32715 A1 | 5/2001 |
| WO | 2004/013409 A1 | 2/2004 |
| WO | 2009/060126 A1 | 5/2009 |
| WO | 2010/045576 A2 | 4/2010 |
| WO | 2010/046532 A1 | 4/2010 |
| WO | 2011/091044 A1 | 7/2011 |
| WO | 2013070969 | 5/2013 |

OTHER PUBLICATIONS

SCHARLAU®, "Technical Data Sheet—Product code: XI0080, D(+)-Xylose, extra pure, Ph, Eur, BP", (Jun. 2006).*
Google Search Results, Searched Dec. 21, 2013, p. 1.*
International Patent Application No. PCT/US2012/067644, International Search Report and Written Opinion, mailed Mar. 13, 2013 (13 pages).
Korean Intellectual Property Office, "International Search Report and Written Opinion" in International Application No. PCT/US2012/067537 (Mar. 18, 2013).
Ioannidou et al., "Direct determination of toxic trace metals in honey and sugars using inductively coupled plasma atomic emission spectrometry," *Talanta*, 65(1): 92-97 (2005).
Kelkone Levai, "Atom spectrometric methods for determination of trace metal impurities in pharmaceutical substances," *Acta Pharmaceutica Hungarica*, 71(3): 350-356 (2001).
Miller-Ihli et al., "Direct determination of lead in sugars using graphite furnace atomic absorption spectrometry," *Atomic Spectroscopy*, 14(4): 85-89 (1993).
Napradean et al., "Studies regarding cadmium determination by atomic absorption spectrometry. Note II. Pharmaceutical finished products," *Farmacia*, 53(2): 86-90 (Bucharest, Romania, 2005).
Pohl et al., "Direct Determination of the Total Concentrations of Magnesium, Calcium, Manganese, and Iron in Addition to their Chemical and Physical Fractions in Dark Honeys," *Anal. Lett.*, 44(13): 2265-2279 (2011).

(Continued)

*Primary Examiner* — David M Brunsman
(74) *Attorney, Agent, or Firm* — Travis B. Gasa; Ballard Spahr LLP

(57) ABSTRACT

Compositions comprising C5 and C6 monosaccharides and low levels of undesirable impurities, such as compounds containing sulfur, nitrogen, or metals, are disclosed.

23 Claims, No Drawings

(56) References Cited

OTHER PUBLICATIONS

Terol et al., "High-Temperature Liquid Chromatography Inductively Coupled Plasma Atomic Emission Spectrometry hyphenation for the combined organic and inorganic analysis of foodstuffs," *J. Chromatography*, 1217(40): 6195-6202 (2010).

Veres et al., "Studies on matrix effects in the determination of the metal content of sugar complexes by atomic absorption spectrometry," *Magyar Kemiai Folyoirat*, 93(5): 199-204 (1987).

Wu et al., "Determination of trace calcium in glucose by Zeeman flame atomic absorption spectrometry," *Guangdong Weiliang Yuansu Kexue*, 14(3): 58-60 (2007).

Korean Intellectual Property Office, "International Search Report and Written Opinion" in International Patent Application No. PCT/US2012/067641 (Mar. 13, 2013).

Korean Intellectual Property Office, "International Search Report and Written Opinion" in International Patent Application No. PCT/US2012/067538 (Mar. 18, 2013).

Scharlau: Technical Data Sheet Product Code GL0125 D(+)-Glucose anhydrous, extra pure, Ph Eur, USP, BP, 2006 (1 page).

Scharlau,: Technical Data Sheet Product Code LE0070 D(−)-Fructose, extra pure, Ph Eur, USP, BP, FCC, Jun. 2006 (1 page).

ASTM D874-13a, "Standard Test Method for Sulfated Ash from Lubricating Oils and Additives", www.astm.org/Standards/D874.htm,Oct. 13, 2013 (2 pages).

U.S. Appl. No. 13/649,294, "Non Final Office Action", mailed Sep. 18, 2013 (18 pages).

U.S. Appl. No. 13/649,343, "Non-Final Office Action", mailed Oct. 8, 2013 (8 pages).

U.S. Appl. No. 13/649,437, "Non Final Office Action", mailed Jul. 26, 2013 (7 pages).

Buranov et al., "Extraction and characterization of hemicelluloses from flax shives by different methods", Carbohydrate Polymers, vol. 79, No. 1, 2010 (pp. 17-25).

Cacace et al., "Pressurized low polarity water extraction of lignans from whole flaxseed", Journal of Food Engineering, vol. 77, No. 4, 2006 (pp. 1087-1095).

Cox et al., "Preparation and characterisation of a carbon adsorbent from flax shive by dehydration with sulfuric acid", Journal of Chemical Technology and Biotechnology, vol. 74, No. 11, 1999 (pp. 1019-1029).

Ranatunga et al., "The effect of overliming on the toxicity of dilute acid pretreated lignocellulosics: the role of inorganics, uronic acids and ether-soluble organics", Enzyme and Microbial Technology, vol. 27, No. 3, 2000 (pp. 240-247).

Sasaki et al., "Dissolution and Hydrolysis of Cellulose in Subcritical and Supercritical Water", Industrial & Engineering Chemistry Research, 39(8), 2000 (pp. 2883-2890).

Schenk, "Glucose and Glucose-Containing Syrups", Ullmann's Encyclopedia of Industrial Chemistry, vol. 17, http://dx.doi.org/10.1002%2F14356007.a12_457.pub2, 2006 (pp. 45-66).

Thomas, "Practical Guide to ICP-MS", Tutorial for Beginners, Second Edition, CRC Press, Print ISBN: 978-1-4200-6786-6, 2008.

Vassilev et al., "An Overview of the Chemical Composition of Biomass", Fuel 89, 2010 (pp. 913-933).

Zhang et al., "Cellodextrin preparation by mixed-acid hydrolysis and chromatographic separation", Analytical Biochemistry, 322(2), 2003 (pp. 225-232).

"Enzyme Technology, Glucose from Cellulose", retrieved from the internet at least as early as Oct. 7, 2013, Http://www.lsbu.ac.uk/water/enztech/cellulose.html, 2 pages.

Finney N. "Essentials of Glycobiology", pp. 1-26; Apr. 2004 (Apr. 1, 2004), http://grtc.ucsd.edu/old_essentials/2004/lecture.pdf.

Official Action issued on Oct. 4, 2013 for Canadian Patent Application No. 2,804,993 filed Dec. 3, 2012 (Applicant—Renmatix, Inc.; Inventors—Floyd, et al.) (3 pages).

Official Action issued on Oct. 1, 2013 for Canadian Patent Application No. 2,817,235 filed Dec. 3, 2012 (Applicant—Renmatix, Inc.; Inventors—Floyd, et al.) (3 pages).

Applicant-Initiated Interview Summary issued on Oct. 17, 2013 for U.S. Appl. No. 13/649,395, filed Oct. 11, 2012 (Applicant—Renmatix, Inc.; ; Inventors—Floyd, et al.) (3 pages).

Applicant-Initiated Interview Summary issued on Oct. 21, 2013 for U.S. Appl. No. 13/349,437, filed Oct. 11, 2012 (Applicant—Renmatix, Inc.; Inventors—Floyd, et al.) (3 pages).

Non-Final Rejection issued on Mar. 3, 2014 for U.S. Appl. No. 13/649,294, filed Oct. 11, 2012 (Applicants—Renmatix, Inc.; Inventors—Floyd et al.) (11 pages).

Non-Final Rejection issued on Mar. 7, 2014 for U.S. Appl. No. 13/649,343, filed Oct. 11, 2012 (Applicants—Renmatix, Inc.; Inventors—Floyd et al.) (22 pages).

Lu, X. & Saka, S. (2010). Hydrolysis of Japanese beech by batch and semi-flow water under subcritical temperatures and pressures. Biomass and bioenergy, 34(8), 1089-1097.

Winter, F., Wartha, C., & Hofbauer, H. (1999). NO and $N_2O$ formation during the combustion of wood, straw, malt waste and peat. Bioresource Technology, 70(1), 39-49.

\* cited by examiner

US 8,894,771 B2

COMPOSITIONS COMPRISING C5 AND C6 MONOSACCHARIDES

CROSS REFERENCE TO RELATED APPLICATIONS

This application claims the benefit of:
U.S. Application No. 61/581,907 filed Dec. 30, 2011;
U.S. Application No. 61/581,922 filed Dec. 30, 2011;
U.S. Application No. 61/581,878 filed Dec. 30, 2011; and
U.S. Application No. 61/581,890 filed Dec. 30, 2011;
the entire disclosures of which are incorporated herein by reference.

FIELD OF THE INVENTION

The present invention generally relates to compositions comprising C5 and C6 monosaccharides containing maximum levels of undesirable impurities, such as compounds containing sulfur, nitrogen, or metals, especially those processed from lignocellulosic biomass using supercritical, subcritical, and/or near critical fluid extraction.

BACKGROUND OF THE INVENTION

There are a number of processes for converting lignocellulosic biomass into liquid streams of various fermentable sugars. Certain preferred processes are based on supercritical water (SCW) or hot compressed water (HCW) technology, which offer several advantages including high throughputs, use of mixed feedstocks, separation of sugars, and avoidance of concentrated acids, microbial cultures, and enzymes. Processes using hot compressed water may have two distinct operations: pre-treatment and cellulose hydrolysis. The pre-treatment process hydrolyzes the hemicellulose component of the lignocellulosic biomass and cellulose hydrolysis (CH) process, as its name infers, hydrolyzes the cellulose fibers. The resultant five carbon (C5) and six carbon (C6) sugar streams are recovered separately. The remaining solids, which consist mostly of lignin, are preferably recovered, such as through filtration, and may be used as a fuel to provide thermal energy to the process itself or for other processes.

Among their many uses, the sugar streams may be converted to ethanol through fermentation using yeast or bacteria that feed on the sugars. As the sugars are consumed, ethanol and carbon dioxide are produced.

The invention is directed to these compositions, as well as and other important ends.

SUMMARY OF THE INVENTION

In a first embodiment, the invention is directed to compositions, comprising C6 monosaccharides. In particular, the compositions comprise:
at least one water-soluble C6 monosaccharide hydrolysate; and
less than about 6750 ppm in total by weight, based on total weight of water-soluble C6 saccharide hydrolysate in said composition, of elements;
wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In certain embodiments, the compositions comprise:
at least one water-soluble C6 monosaccharide hydrolysate;
less than about 10 ppm by weight, based on total weight of water-soluble C6 saccharide hydrolysate in said composition, of aluminum;
less than about 350 ppm by weight, based on total weight of water-soluble C6 saccharide hydrolysate in said composition, of calcium;
less than about 425 ppm by weight, based on total weight of water-soluble C6 saccharide hydrolysate in said composition, of iron; and
less than about 4500 ppm by weight, based on total weight of water-soluble C6 saccharide hydrolysate in said composition, of sulfur.

In certain embodiments, the compositions comprise:
at least one water-soluble C6 monosaccharide hydrolysate; and
less than about 10 ppm by weight, based on total weight of water-soluble C6 saccharide hydrolysate in said composition, of aluminum.

In certain embodiments, the compositions comprise:
at least one water-soluble C6 monosaccharide hydrolysate; and
less than about 350 ppm by weight, based on total weight of water-soluble C6 saccharide hydrolysate in said composition, of calcium.

In certain embodiments, the compositions comprise:
at least one water-soluble C6 monosaccharide hydrolysate; and
less than about 425 ppm by weight, based on total weight of water-soluble C6 saccharide hydrolysate in said composition, of iron.

In certain embodiments, the compositions comprise:
at least one water-soluble C6 monosaccharide hydrolysate; and
less than about 4500 ppm by weight, based on total weight of water-soluble C6 saccharide hydrolysate in said composition, of sulfur.

In other embodiments, the invention is directed to compositions, comprising C5 monosaccharides. In particular, the compositions comprise:
at least one water-soluble C5 monosaccharide hydrolysate; and
less than about 1950 ppm in total by weight, based on total weight of water-soluble C5 saccharide hydrolysate in said composition, of elements;
wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In certain embodiments, the compositions comprise:
at least one water-soluble C5 monosaccharide hydrolysate;
less than about 5 ppm by weight, based on total weight of water-soluble C5 saccharide hydrolysate in said composition, of aluminum;
less than about 300 ppm by weight, based on total weight of water-soluble C5 saccharide hydrolysate in said composition, of calcium;
less than about 10 ppm by weight, based on total weight of water-soluble C5 saccharide hydrolysate in said composition, of iron; and
less than about 1000 ppm by weight, based on total weight of water-soluble C5 saccharide hydrolysate in said composition, of sulfur.

In certain embodiments, the compositions comprise:
at least one water-soluble C5 monosaccharide hydrolysate; and
less than about 5 ppm by weight, based on total weight of water-soluble C5 saccharide hydrolysate in said composition, of aluminum.

In certain embodiments, the compositions comprise:
at least one water-soluble C5 monosaccharide hydrolysate; and less than about 300 ppm by weight, based on total weight of water-soluble C5 saccharide hydrolysate in said composition, of calcium.

In certain embodiments, the compositions comprise:
at least one water-soluble C5 monosaccharide hydrolysate; and
less than about 10 ppm by weight, based on total weight of water-soluble C5 saccharide hydrolysate in said composition, of iron.

In certain embodiments, the compositions comprise:
at least one water-soluble C5 monosaccharide hydrolysate; and
less than about 1000 ppm by weight, based on total weight of water-soluble C5 saccharide hydrolysate in said composition, of sulfur.

In certain embodiments, the invention is directed to methods of reducing the level of enzyme required for enzymatically hydrolyzing first water-soluble C6 saccharides having an average degree of polymerization to about 2 to about 15, preferably about 2 to about 10, and more preferably about 2 to about 6, to second water-soluble C6 saccharides having a lower average degree of polymerization than said average degree of polymerization of said first water-soluble C6 saccharides, comprising:
providing a hydrolysate comprising said first water-soluble C6 saccharides and less than about 5250 ppm in total by weight, based on total weight of water-soluble C6 saccharide hydrolysate in said composition, of elements;
wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In certain embodiments, the invention is directed to methods of reducing the level of enzyme required for enzymatically hydrolyzing first water-soluble C5 saccharides having an average degree of polymerization to about 2 to about 28, preferably about 2 to about 15, more preferably about 2 to about 13, even more preferably about 2 to about 6, to second water-soluble C5 saccharides having a lower average degree of polymerization than said average degree of polymerization of said first water-soluble C5 saccharides, comprising:
providing a hydrolysate comprising said first water-soluble C5 saccharides and less than about 3700 ppm in total by weight, based on total weight of water-soluble C5 saccharide hydrolysate in said composition, of elements;
wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

DETAILED DESCRIPTION OF THE INVENTION

As employed above and throughout the disclosure, the following terms, unless otherwise indicated, shall be understood to have the following meanings.

As used herein, the singular forms "a," "an," and "the" include the plural reference unless the context clearly indicates otherwise.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

As used herein, the phrase "substantially free" means have no more than about 1%, preferably less than about 0.5%, more preferably, less than about 0.1%, by weight of a component, based on the total weight of any composition containing the component.

A supercritical fluid is a fluid at a temperature above its critical temperature and at a pressure above its critical pressure. A supercritical fluid exists at or above its "critical point," the point of highest temperature and pressure at which the liquid and vapor (gas) phases can exist in equilibrium with one another. Above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good solvation.

Reported critical temperatures and pressures include: for pure water, a critical temperature of about 374.2° C., and a critical pressure of about 221 bar; for carbon dioxide, a critical temperature of about 31° C. and a critical pressure of about 72.9 atmospheres (about 1072 psig). Near critical water has a temperature at or above about 300° C. and below the critical temperature of water (374.2° C.), and a pressure high enough to ensure that all fluid is in the liquid phase. Sub-critical water has a temperature of less than about 300° C. and a pressure high enough to ensure that all fluid is in the liquid phase. Sub-critical water temperature may be greater than about 250° C. and less than about 300° C., and in many instances sub-critical water has a temperature between about 250° C. and about 280° C. The term "hot compressed water" is used interchangeably herein for water that is at or above its critical state, or defined herein as near-critical or sub-critical, or any other temperature above about 50° C. (preferably, at least about 100° C.) but less than subcritical and at pressures such that water is in a liquid state As used herein, a fluid which is "supercritical" (e.g. supercritical water, supercritical $CO_2$, etc.) indicates a fluid which would be supercritical if present in pure form under a given set of temperature and pressure conditions. For example, "supercritical water" indicates water present at a temperature of at least about 374.2° C. and a pressure of at least about 221 bar, whether the water is pure water, or present as a mixture (e.g. water and ethanol, water and $CO_2$, etc). Thus, for example, "a mixture of sub-critical water and supercritical carbon dioxide" indicates a mixture of water and carbon dioxide at a temperature and pressure above that of the critical point for carbon dioxide but below the critical point for water, regardless of whether the supercritical phase contains water and regardless of whether the water phase contains any carbon dioxide. For example, a mixture of sub-critical water and supercritical $CO_2$ may have a temperature of about 250° C. to about 280° C. and a pressure of at least about 225 bar.

As used herein, "lignocellulosic biomass or a component part thereof" refers to plant biomass containing cellulose, hemicellulose, and lignin from a variety of sources, including, without limitation (1) agricultural residues (including corn stover and sugarcane bagasse), (2) dedicated energy crops, (3) wood residues (including hardwoods, softwoods, sawmill and paper mill discards), and (4) municipal waste, and their constituent parts including without limitation, lignocellulose biomass itself, lignin, $C_6$ saccharides (including cellulose, cellobiose, $C_6$ oligosaccharides, $C_6$ monosaccharides, $C_5$ saccharides (including hemicellulose, $C_5$ oligosaccharides, and $C_5$ monosaccharides), and mixtures thereof.

As used herein, "ash" refers to the non-aqueous residue that remains after a sample is burned, and consists mostly of metal oxides. Ash content may be measured in accordance with ASTM Standard Method No. E1755-01 "Standard Method for the Determination of Ash in Biomass." This test method covers the determination of ash, expressed as the percentage of residue remaining after dry oxidation at 550 to 600° C. All results are reported relative to the 105° C. oven dry weight of the sample." See also: http://www.nrel.gov/biomass/pdfs/42622.pdf and http://www.astm.org/Standards/E1755.htm, which are both incorporated herein by reference in their entirety.

As used herein, "degree of polymerization" refers to the number of monomeric units in a macromolecule or polymer or oligomer molecule, including those monomeric units that are not identical (such as in a oligomer with different monomeric residues). The degree of polymerization (DP) of the various saccharides in the compositions of the invention may be measured using gel permeation chromatography (GPC), high pressure liquid chromatography (HPLC), such as DIONEX with an electrochemical detector, matrix-assisted laser desorption/ionization time-of-flight (MALDI-TOF) mass spectrometry, or other conventional molecular weight determination methods.

C6 Monosaccharides

Accordingly, in one embodiment, the invention is directed to compositions, comprising C6 monosaccharides. In particular embodiments, the compositions comprise:

at least one water-soluble C6 monosaccharide hydrolysate; and less than about 6750 ppm in total by weight, based on total weight of water-soluble C6 saccharide hydrolysate in said composition, of elements;

wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In certain preferred embodiments, said elements are present at a level of less than about 6600 ppm in total by weight, based on total weight of water-soluble C6 saccharide hydrolysate in said composition, of said elements.

In certain embodiments, the compositions comprise:
at least one water-soluble C6 monosaccharide hydrolysate;
less than about 10 ppm by weight, based on total weight of water-soluble C6 saccharide hydrolysate in said composition, of aluminum;
less than about 350 ppm by weight, based on total weight of water-soluble C6 saccharide hydrolysate in said composition, of calcium;
less than about 425 mg, based on total weight of water-soluble C6 saccharide hydrolysate in said composition, of iron; and
less than about 4500 ppm by weight, based on total weight of water-soluble C6 saccharide hydrolysate in said composition, of sulfur.

In certain embodiments, the compositions comprise:
at least one water-soluble C6 monosaccharide hydrolysate; and
less than about 10 ppm by weight, based on total weight of water-soluble C6 saccharide hydrolysate in said composition, of aluminum.

In certain embodiments, the compositions comprise:
at least one water-soluble C6 monosaccharide hydrolysate; and
less than about 350 ppm by weight, based on total weight of water-soluble C6 saccharide hydrolysate in said composition, of calcium.

In certain embodiments, the compositions comprise:
at least one water-soluble C6 monosaccharide hydrolysate; and
less than about 425 mg, based on total weight of water-soluble C6 saccharide hydrolysate in said composition, of iron.

In certain embodiments, the compositions comprise:
at least one water-soluble C6 monosaccharide hydrolysate; and
less than about 4500 ppm by weight, based on total weight of water-soluble C6 saccharide hydrolysate in said composition, of sulfur.

In certain preferred embodiments of the compositions comprising the water-soluble C6 monosaccharide hydrolysate, the compositions comprise:
less than about 6750 ppm in total by weight, based on total weight of water-soluble C6 saccharide hydrolysate in said composition, of elements;
wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In certain preferred embodiments, said elements are present at a level of less than about 6600 ppm in total by weight, based on total weight of water-soluble C6 saccharide hydrolysate in said composition, of said elements.

In certain embodiments, the water-soluble C6 monosaccharide hydrolysate is extracted from lignocellulosic biomass. In certain embodiments, the water-soluble C6 monosaccharide hydrolysate is processed from lignocellulosic biomass using supercritical, subcritical, or near critical fluid extraction, or a combination thereof.

In certain embodiments, the compositions further comprise water.

In certain embodiments, the water-soluble C6 monosaccharide hydrolysate is present at a concentration of at least about 0.5 g/L.

In certain embodiments, the C6 monosaccharide is glucose, galactose, mannose, fructose, or a mixture thereof.

In certain preferred embodiments of the compositions comprising the water-soluble C6 monosaccharide hydrolysate, the compositions further comprise less than about 10 ppm by weight, based on total weight of water-soluble C6 saccharide hydrolysate in said composition, of aluminum, preferably less than about 7.5 ppm by weight, based on total weight of water-soluble C6 saccharide hydrolysate in said composition, of aluminum.

In certain preferred embodiments of the compositions comprising the water-soluble C6 monosaccharide hydrolysate, the compositions further comprise less than about 350 ppm by weight, based on total weight of water-soluble C6 saccharide hydrolysate in said composition, of calcium, preferably less than about 325 ppm by weight, based on total weight of water-soluble C6 saccharide hydrolysate in said composition, of calcium.

In certain preferred embodiments of the compositions comprising the water-soluble C6 monosaccharide hydrolysate, the compositions further comprise less than about 425 ppm by weight, based on total weight of water-soluble C6 saccharide hydrolysate in said composition, of iron, preferably less than about 420 ppm by weight, based on total weight of water-soluble C6 saccharide hydrolysate in said composition, of iron.

In certain preferred embodiments of the compositions comprising the water-soluble C6 monosaccharide hydrolysate, the compositions further comprise less than about 4500 ppm by weight, based on total weight of water-soluble C6 saccharide hydrolysate in said composition, of sulfur, preferably less than about 4425 ppm by weight, based on total weight of water-soluble C6 saccharide hydrolysate in said composition, of sulfur.

In certain preferred embodiments of the compositions comprising the water-soluble C6 monosaccharide hydrolysate, the weight ratio of said water-soluble C6 monosaccharide hydrolysate to said elements is greater than about 25:1, preferably greater than about 30:1.

In certain preferred embodiments of the compositions comprising the water-soluble C6 monosaccharide hydrolysate, the compositions further comprise at least one water-soluble C6 oligosaccharide having a degree of polymerization of about 2 to about 15, preferably about 2 to about 13, more preferably about 2 to about 10, and even more preferably about 2 to 6.

In certain preferred embodiments of the compositions comprising the water-soluble C6 monosaccharide hydrolysate, the compositions further comprise at least one water-soluble C5 saccharide having a degree of polymerization of about 1 to about 28, preferably about 1 to 15, more preferably about 1 to about 10, and even more preferably about 1 to about 6.

In certain embodiments, the water-soluble C6 monosaccharide hydrolysate is processed from lignocellulosic biomass using supercritical, subcritical, or near critical fluid extraction, or a combination thereof.

In certain embodiments, the level of said elements are measured by inductively coupled plasma emission spectroscopy.

In other embodiments, the compositions comprise less than about 1500 mg of nitrogen per kg of total weight of water-soluble C6 saccharides, preferably less than about 1450 mg of nitrogen per kg of total weight of water-soluble C6 saccharides. Nitrogen may be measured by thermal conductivity detection after combustion and reduction.

In yet other embodiments, the compositions further comprise a weight ratio of the total mass of hydrogen and nitrogen to carbon of less than about 0.17.

In certain other embodiments, the compositions comprising the C6 monosaccharides further comprise less than a maximum of any of the elements, individually or in combination, in the table listed below:

| Element | Level less than about (ppm or mg of element/kg of C6 saccharides) |
| --- | --- |
| As | 0.25 |
| B | 1.0 |
| Ba | 1.0 |
| Be | 0.1 |
| Cd | 0.1 |
| Co | 0.25 |
| Cr | 3.25 |
| Cu | 325 |
| K | 350 |
| Li | 25 |
| Mg | 0.1 |
| Mn | 625 |
| Mo | 3.0 |
| Na | 15 |
| Ni | 0.25 |
| P | 0.25 |
| Pb | 0.35 |
| Sb | 0.25 |
| Se | 2.0 |
| Si | 0.1 |
| Sn | 0.3 |
| Sr | 0.1 |
| Ti | 0.25 |
| Tl | 1.0 |
| V | 1.0 |
| Zn | 0.1 |

C5 Monosaccharides

Accordingly, in one embodiment, the invention is directed to compositions, comprising C5 monosaccharides. In particular, the compositions comprise:

at least one water-soluble C5 monosaccharide hydrolysate; and less than about 1950 ppm in total by weight, based on total weight of water-soluble C5 saccharide hydrolysate in said composition, of elements;

wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In certain preferred embodiments, the elements are present at a level of less than about 1925 ppm in total by weight, based on total weight of water-soluble C5 saccharide hydrolysate in said composition.

In certain embodiments, the compositions comprise:
at least one water-soluble C5 monosaccharide hydrolysate;
less than about 5 ppm by weight, based on total weight of water-soluble C5 saccharide hydrolysate in said composition, of aluminum;
less than about 300 ppm by weight, based on total weight of water-soluble C5 saccharide hydrolysate in said composition, of calcium;
less than about 10 mg, based on total weight of water-soluble C5 saccharide hydrolysate in said composition, of iron; and
less than about 1000 ppm by weight, based on total weight of water-soluble C5 saccharide hydrolysate in said composition, of sulfur.

In certain embodiments, the compositions comprise:
at least one water-soluble C5 monosaccharide hydrolysate; and
less than about 5 ppm by weight, based on total weight of water-soluble C5 saccharide hydrolysate in said composition, of aluminum.

In certain embodiments, the compositions comprise:
at least one water-soluble C5 monosaccharide hydrolysate; and
less than about 300 ppm by weight, based on total weight of water-soluble C5 saccharide hydrolysate in said composition, of calcium.

In certain embodiments, the compositions comprise:
at least one water-soluble C5 monosaccharide hydrolysate; and
less than about 10 mg, based on total weight of water-soluble C5 saccharide hydrolysate in said composition, of iron.

In certain embodiments, the compositions comprise:
at least one water-soluble C5 monosaccharide hydrolysate; and
less than about 1000 ppm by weight, based on total weight of water-soluble C5 saccharide hydrolysate in said composition, of sulfur.

In certain embodiments, the compositions further comprise:
less than about 1950 ppm in total by weight, based on total weight of water-soluble C5 saccharide hydrolysate in said composition, of elements;
wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In certain preferred embodiments, the elements are present at a level of less than about 1925 ppm in total by weight, based on total weight of water-soluble C5 saccharide hydrolysate in said composition.

In certain preferred embodiments of the compositions comprising the water-soluble C5 monosaccharide hydrolysate, the compositions further comprise less than about 5 ppm by weight, based on total weight of water-soluble C5 saccharide hydrolysate in said composition, of aluminum, preferably less than about 2 ppm by weight, based on total weight of water-soluble C5 saccharide hydrolysate in said composition, of aluminum.

In certain preferred embodiments of the compositions comprising the water-soluble C5 monosaccharide hydrolysate, the compositions further comprise less than about 300 ppm by weight, based on total weight of water-soluble C5 saccharide hydrolysate in said composition, of calcium, preferably less than about 280 ppm by weight, based on total weight of water-soluble C5 saccharide hydrolysate in said composition, of calcium.

In certain preferred embodiments of the compositions comprising the water-soluble C5 monosaccharide hydrolysate, the compositions further comprise less than about 10 ppm by weight, based on total weight of water-soluble C5 saccharide hydrolysate in said composition, of iron, preferably less than about 5 ppm by weight, based on total weight of water-soluble C5 saccharide hydrolysate in said composition, of iron.

In certain preferred embodiments of the compositions comprising the water-soluble C5 monosaccharide hydrolysate, the compositions further comprise less than about 1000 ppm by weight, based on total weight of water-soluble C5 saccharide hydrolysate in said composition, of sulfur, preferably less than about 975 ppm by weight, based on total weight of water-soluble C5 saccharide hydrolysate in said composition, of sulfur.

In certain preferred embodiments, the weight ratio of said C5 monosaccharide to said elements is greater than about 90:1, preferably greater than about 95:1.

In certain embodiments, the compositions further comprise water.

In certain embodiments, the water-soluble C5 monosaccharide hydrolysate is present at a concentration of at least 0.5 g/L.

In certain embodiments, the C5 monosaccharide is xylose, arabinose, lyxose, ribose, or a mixture thereof.

In certain preferred embodiments of the compositions comprising the water-soluble C5 monosaccharide hydrolysate, the compositions further comprise at least one water-soluble C5 oligosaccharide having a degree of polymerization of about 2 to about 28, preferably about 2 to about 15, more preferably about 2 to about 10, and even more preferably about 2 to 6.

In certain preferred embodiments of the compositions comprising the water-soluble C5 monosaccharide hydrolysate, the compositions further comprise at least one water-soluble C6 saccharide having a degree of polymerization of about 1 to about 15, preferably about 1 to 13, more preferably about 1 to about 10, and even more preferably about 1 to about 6.

In certain preferred embodiments of the compositions comprising the water-soluble C5 monosaccharide hydrolysate, the compositions further comprise at least one water-soluble C6 saccharide having a degree of polymerization of about 1 to about 15, preferably about 1 to about 13, more preferably about 1 to about 10, and even more preferably about 1 to 6.

In certain embodiments, the water-soluble C5 monosaccharide hydrolysate is processed from lignocellulosic biomass using supercritical, subcritical, or near critical fluid extraction, or a combination thereof.

In certain embodiments, the level of said elements are measured by inductively coupled plasma emission spectroscopy.

In other embodiments, the compositions comprise less than about 350 mg of nitrogen per kg of total weight of water-soluble C5 saccharides, preferably less than about 325 mg of nitrogen per kg of total weight of water-soluble C5 saccharides. Nitrogen may be measured by thermal conductivity detection after combustion and reduction.

In yet other embodiments, the compositions further comprise a weight ratio of the total mass of hydrogen and nitrogen to carbon of less than about 0.17. Carbon, hydrogen, and nitrogen levels may be measured by thermal conductivity detection after combustion and reduction.

In certain other embodiments, the compositions comprising the C5 monosaccharides further comprise less than a maximum of any of the elements, individually or in combination, in the table listed below:

| Element | Level less than about (ppm or mg of element/kg of C5 saccharides) |
| --- | --- |
| As | 0.2 |
| B | 1.0 |
| Ba | 0.25 |
| Be | 0.1 |
| Cd | 0.1 |
| Co | 0.1 |
| Cr | 0.1 |
| Cu | 275 |
| K | 325 |
| Li | 75 |
| Mg | 0.2 |
| Mn | 35 |
| Mo | 0.25 |
| Na | 20 |
| Ni | 0.25 |
| P | 0.15 |
| Pb | 0.25 |
| Sb | 0.20 |
| Se | 3.0 |
| Si | 0.1 |
| Sn | 0.25 |
| Sr | 0.1 |

-continued

| Element | Level less than about (ppm or mg of element/kg of C5 saccharides) |
|---|---|
| Ti | 4.0 |
| Tl | 0.25 |
| V | 1.25 |
| Zn | 0.25 |

Further Embodiments

In further embodiments, the compositions further comprise less than about 0.5% by weight, based on the total weight of said C5 monosaccharides or C6 monosaccharides, of organic solvent, such as alcohols, including water miscible lower aliphatic $C_1$-$C_4$ alcohols (e.g., methanol, ethanol, isopropanol, t-butanol). In preferred embodiments, the compositions contain less than about 0.1% by weight, based on the total weight of said of said C5 monosaccharides or C6 monosaccharides of organic solvent. In more preferred embodiments, the compositions contain substantially no organic solvent.

The compositions of the invention are preferably prepared from biomass by processes employing supercritical, subcritical, and/or near critical water, preferably without the addition of acid. The processes may include pretreatment step or steps using supercritical or near critical water to separate the C5 sugars (monomers and/or oligomers) from cellulose and lignin. In the pretreatment step, suitable temperatures are about 130° C. to about 250° C., suitable pressures are about 4 bars to about 100 bars, and suitable residence times are about 0.5 minutes to about 5 hours. The processes may also include a cellulose hydrolysis step or steps using supercritical or near critical water to separate the cellulose (which may processed to form C6 monomeric and/or oligomeric sugars) from the lignin. In the hydrolysis step(s), suitable temperatures are about 250° C. to about 450° C., suitable pressures are about 40 bars to about 260 bars, and suitable residence times are about 0.1 seconds to about 3 minutes. The C5 monomers in the pretreatment step are formed by autohydrolysis both from xylan directly and/or from C5 oligomers. Similarly, the C6 monomers are formed in the supercritical hydrolysis step directly from the cellulose and/or from C6 oligomers. The pretreatment step also produces small amounts of C6 sugars in oligomeric and/or monomeric form. The C5 and C6 oligomers may be hydrolyzed to their respective monomers using acid, such as sulfuric acid. The compositions may be prepared in any suitable reactor, including, but not limited to, a tubular reactor, a digester (vertical, horizontal, or inclined), or the like. Suitable digesters include the digester system described in U.S. Pat. No. 8,057,639, which include a digester and a steam explosion unit, the entire disclosure of which is incorporated by reference.

The compositions of the invention comprising C5 monosaccharides or C6 monosaccharides may be utilized in a wide variety of applications, where C5 and C6 sugars are conventionally utilized, including, but not limited to, the production of various chemicals and fuels using fermentative, enzymatic, catalytic, and non-catalytic (e.g., thermal decomposition) processes. Such processes are useful for preparing feedstocks for the preparation of the following non-exhaustive list:

fuels (such as gasoline, jet fuel, butanol, and the like);
chemicals (such as acetic acid, acetic anhydride, acetone, acrylic acid, adipic acid, benzene, ethanol, ethylene, ethylene glycol, ethylene oxide, methanol, polypropylene, terephthalic acid, toluene, xylene, 1,3-propanediol, 1,4-butanediol, and the like);

pharmaceuticals and foods (such as acetoin, alanine, arabitol, ascorbic acid, aspartic acid, citric acid, coumaric acid, fumaric acid, glycerol, glycine, kojic acid, lactic acid, lysine, malonic acid, proline, propionic acid, serine, sorbitol, succinic acid, threonine, xylitol, sugar acids (glucaric acid, gluconic acid, xylonic acids), and the like);

specialty chemicals (such as acontic acid, glutamic acid, malic acid, oxalic acid, and the like);

textile applications (such as formic acid and the like); and
industrial intermediates (acetaldehyde, 3-hydroxypropionic acid, 2,5-furan dicarboxylic acid, furfural, glutaric acid, itaconic acid, levulinic acid, and the like).

In certain embodiments, the invention is directed to methods of reducing the level of enzyme required for enzymatically hydrolyzing first water-soluble C6 saccharides having an average degree of polymerization to about 2 to about 15, preferably about 2 to about 10, and more preferably about 2 to about 6, to second water-soluble C6 saccharides having a lower average degree of polymerization than said average degree of polymerization of said first water-soluble C6 saccharides, comprising:

providing a hydrolysate comprising said first water-soluble C6 saccharides and less than about 5250 ppm in total by weight, based on total weight of water-soluble C6 saccharide hydrolysate in said composition, of elements;

wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In certain embodiments, the C6 saccharides are extracted from lignocellulosic biomass. In other embodiments, the C6 saccharides are processed from lignocellulosic biomass using supercritical, subcritical, or near critical fluid extraction, or a combination thereof.

In certain embodiments, the invention is directed to methods of reducing the level of enzyme required for enzymatically hydrolyzing first water-soluble C5 saccharides having an average degree of polymerization to about 2 to about 28, preferably about 2 to about 15, more preferably about 2 to about 13, even more preferably about 2 to about 6, to second water-soluble C5 saccharides having a lower average degree of polymerization than said average degree of polymerization of said first water-soluble C5 saccharides, comprising:

providing a hydrolysate comprising said first water-soluble C5 saccharides and less than about 3700 ppm in total by weight, based on total weight of water-soluble C5 saccharide hydrolysate in said composition, of elements;

wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In certain embodiments, the C5 saccharides are extracted from lignocellulosic biomass. In other embodiments, the C5 saccharides are processed from lignocellulosic biomass using supercritical, subcritical, or near critical fluid extraction, or a combination thereof.

The present invention is further defined in the following Examples, in which all parts and percentages are by weight, unless otherwise stated. It should be understood that these examples, while indicating preferred embodiments of the invention, are given by way of illustration only and are not to be construed as limiting in any manner. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Preparation of Monosaccharide Compositions

The C5 monosaccharide and C6 monosaccharide compositions of the invention were prepared using supercritical, subcritical, and near critical water extraction in a two stage process followed by acid hydrolysis. Particulate lignocellulosic biomass consisting of mixed hardwood chips of 140 mesh or less was mixed with water to form a slurry (about 20% by weight solids). The slurry was heated to a temperature of about 170-245° C. and then feed into a pretreatment reactor for about 1-120 minutes under sufficient pressure to keep the water in the liquid phase. The pretreated slurry was then cooled to a temperature less than about 100° C. under little (less than about 10 bar) or no pressure. The pretreated solids were then separated from the liquid stream using a filter press. Alternatively, the solids may be separated using a centrifugal filter pressor. The pretreated solids were then mixed with water to form a slurry and the slurry was heated to a temperature of about 150-250° C. The slurry was then subjected to supercritical water at about 374-600° C. in a hydrolysis reactor for about 0.05-10 seconds under a pressure of about 230-300 bar. After exiting the hydrolysis reactor, the hydrolyzed slurry was quenched with water and then flashed to about ambient temperature and pressure to remove water. The lignin solids were then separated from the liquid stream using a centrifugal decanter and air dried.

The C5 oligosaccharides and the C6 oligosaccharides streams were first concentrated to about 200 g/L, adjusted to about pH 3-4 and filtered using 0.45 micron filter.

Sulfuric acid (0.3%) was added to the C5 oligosaccharides and the C6 oligosaccharides streams in a tubular reactor at a residence time of about 1 minute at about 200° C. to hydrolyze the oligosaccharides to their respective monosaccharides. Alternatively, a batch autoclave at a lower temperature or a continuously stirred agitated tank reactor may be used. The glucose was cleaned with over liming and had acetic acid at a level of less than about 5 g/L. The xylose was cleaned by contacting it with ion exchange resin and had acetic acid at a level of less than about 5 g/L.

Example 2

Analysis of Monosaccharide Compositions Using Inductively Coupled Plasma

The dried compositions containing the C5 and C6 monosaccharides of Example 1 were analyzed using inductively coupled plasma emission spectroscopy. The results are shown in the table below:

| Species | Monosaccharide (glucose sample) g/liter or ppm based on total C6 saccharides | Monosaccharide (xylose sample) g/liter or ppm based on total C5 saccharides |
|---|---|---|
| Al | 7.40 | 0.39 |
| As | 0.18 | 0.12 |
| B | 0.81 | 0.91 |
| Ba | 0.78 | 0.16 |
| Be | 0.00 | 0.00 |
| Ca | 0.08 | 0.02 |
| Cd | 0.07 | 0.02 |
| Co | 0.18 | 0.04 |
| Cr | 3.09 | 0.08 |
| Cu | 316.00 | 261.00 |
| Fe | 0.05 | 0.03 |
| K | 333.00 | 291.00 |
| Li | 19.50 | 60.00 |
| Mg | 0.03 | 0.12 |
| Mn | 590.00 | 33.60 |
| Mo | 2.09 | 0.18 |
| Na | 13.50 | 17.90 |
| Ni | 0.12 | 0.08 |
| P | 0.15 | 0.07 |
| Pb | 0.24 | 0.16 |
| S | 54.50 | 10.80 |
| Sb | 0.20 | 0.14 |
| Se | 1.61 | 2.48 |
| Si | 0.00 | 0.00 |
| Sn | 0.24 | 0.16 |
| Sr | 0.00 | 0.00 |
| Ti | 88.90 | 3.56 |
| Tl | 0.18 | 0.12 |
| V | 0.81 | 0.91 |
| Zn | 0.78 | 0.16 |

When ranges are used herein for physical properties, such as molecular weight, or chemical properties, such as chemical formulae, all combinations, and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A composition, comprising:
    at least one water-soluble C5 monosaccharide hydrolysate;
    at least one water-soluble C5 oligosaccharide hydrolysate having a degree of polymerization of about 2 to about 15; and
    impurities; wherein said impurities comprise:
        less than about 1950 ppm in total by weight, based on total weight of water-soluble C5 saccharide hydrolysate in said composition, of elements;
        wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

2. A composition of claim 1,
    wherein said water-soluble C5 monosaccharide hydrolysate is extracted from lignocellulosic biomass.

3. A composition of claim 2,
    wherein said water-soluble C5 monosaccharide hydrolysate is processed from lignocellulosic biomass using supercritical, subcritical, or near critical fluid extraction, or a combination thereof.

4. A composition of claim 1, further comprising:
water.

5. A composition of claim 1,
wherein said water-soluble C5 monosaccharide hydrolysate is present at a concentration of at least 0.5 g/L.

6. A composition of claim 1,
wherein said water-soluble C5 monosaccharide hydrolysate is xylose, arabinose, lyxose, ribose, or a mixture thereof.

7. A composition of claim 1, further comprising:
less than about 5 ppm by weight, based on total weight of water-soluble C5 saccharide hydrolysate in said composition, of aluminum.

8. A composition of claim 1, further comprising:
less than about 300 ppm by weight, based on total weight of water-soluble C5 saccharide hydrolysate in said composition, of calcium.

9. A composition of claim 1, further comprising:
less than about 10 ppm by weight, based on total weight of water-soluble C5 saccharide hydrolysate in said composition, of iron.

10. A composition of claim 1, further comprising:
less than about 1000 ppm by weight, based on total weight of water-soluble C5 saccharide hydrolysate in said composition, of sulfur.

11. A composition of claim 1,
wherein the weight ratio of said water-soluble C5 monosaccharide hydrolysate to said elements is greater than about 90:1.

12. A composition of claim 1,
wherein the level of said elements is measured by inductively coupled plasma emission spectroscopy.

13. A composition of claim 1, further comprising:
less than about 350 mg of nitrogen per kg of total weight of water-soluble C5 saccharide hydrolysate.

14. A composition of claim 1, further comprising:
a weight ratio of the total mass of hydrogen and nitrogen to carbon of less than about 0.17.

15. A composition of claim 1, further comprising:
at least one water-soluble C6 saccharide having a degree of polymerization of about 1 to about 15.

16. A composition of claim 1,
wherein said at least one water-soluble C5 oligosaccharide hydrolysate has a degree of polymerization of about 2 to about 6.

17. A composition, comprising:
at least one water-soluble C5 monosaccharide hydrolysate;
at least one water-soluble C5 oligosaccharide hydrolysate having a degree of polymerization of about 2 to about 15; and
impurities; wherein said impurities comprise:
less than about 5 ppm by weight, based on total weight of water-soluble C5 saccharide hydrolysate in said composition, of aluminum;
less than about 300 ppm by weight, based on total weight of water-soluble C5 saccharide hydrolysate in said composition, of calcium;
less than about 10 ppm, based on total weight of water-soluble C5 saccharide hydrolysate in said composition, of iron; and
less than about 1000 ppm by weight, based on total weight of water-soluble C5 saccharide hydrolysate in said composition, of sulfur.

18. A composition of claim 17, further comprising:
less than about 1950 ppm in total by weight, based on total weight of water-soluble C5 saccharide hydrolysate in said composition, of elements;
wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

19. A composition of claim 17, further comprising:
at least one water-soluble C6 saccharide having a degree of polymerization of about 1 to about 15.

20. A composition, comprising:
at least one water-soluble C5 monosaccharide hydrolysate;
at least one water-soluble C5 oligosaccharide hydrolysate having a degree of polymerization of about 2 to about 15; and
impurities; wherein said impurities comprise:
less than about 5 ppm by weight, based on total weight of water-soluble C5 saccharide hydrolysate in said composition, of aluminum.

21. A composition, comprising:
at least one water-soluble C5 monosaccharide hydrolysate;
at least one water-soluble C5 oligosaccharide hydrolysate having a degree of polymerization of about 2 to about 15; and
impurities; wherein said impurities comprise:
less than about 300 ppm by weight, based on total weight of water-soluble C5 saccharide hydrolysate in said composition, of calcium.

22. A composition, comprising:
at least one water-soluble C5 monosaccharide hydrolysate;
at least one water-soluble C5 oligosaccharide hydrolysate having a degree of polymerization of about 2 to about 15; and
impurities; wherein said impurities comprise:
less than about 10 ppm by weight, based on total weight of water-soluble C5 saccharide hydrolysate in said composition, of iron.

23. A composition, comprising:
at least one water-soluble C5 monosaccharide hydrolysate;
at least one water-soluble C5 oligosaccharide hydrolysate having a degree of polymerization of about 2 to about 15; and
impurities; wherein said impurities comprise
less than about 1000 ppm by weight, based on total weight of water-soluble C5 saccharide hydrolysate in said composition, of sulfur.

* * * * *